(12) United States Patent
Shepherd et al.

(10) Patent No.: US 6,263,223 B1
(45) Date of Patent: Jul. 17, 2001

(54) METHOD FOR MONITORING ARTERIAL OXYGEN SATURATION

(75) Inventors: John M. Shepherd; Steven C. Walker, both of San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/389,352

(22) Filed: Sep. 3, 1999

Related U.S. Application Data (60) Provisional application No. 60/099,579, filed on Sep. 9, 1998, provisional application No. 60/101,079, filed on Sep. 18, 1998, and provisional application No. 60/101,143, filed on Sep. 18, 1998.

(51) Int. Cl.[7] .................................................. A61B 5/00
(52) U.S. Cl. ................................................................ 600/340
(58) Field of Search ................................... 600/310, 322, 600/323, 24, 325, 326, 327, 331, 332, 339, 340, 341, 342, 344

(56) References Cited

U.S. PATENT DOCUMENTS

| | | |
|---|---|---|
| 2,669,988 | 2/1954 | Carpenter . |
| 2,882,893 | 4/1959 | Godfroy . |
| 3,908,665 | 9/1975 | Moses . |

(List continued on next page.)

FOREIGN PATENT DOCUMENTS

| | | |
|---|---|---|
| 4 42 260A1 | 5/1996 | (DE) . |
| WO 86/00207 | 1/1986 | (WO) . |
| WO 90/01293 | 2/1990 | (WO) . |
| WO 90/07907 | 7/1990 | (WO) . |
| WO 6/29927 | 10/1996 | (WO) . |
| WO 96/31155 | 10/1996 | (WO) . |
| WO 97/42903 | 11/1997 | (WO) . |

OTHER PUBLICATIONS

Hayes, et al., "Quantitative Investigation of Artefact in Photoplethysmography and Pulse Oximetry for Respiratory Exercise Testing," Aug. 27, 1998, Web Article: http://www.lut.ac.uk/departments/el/research/optics/ppgraphy/paper2c.htm.

Anonymous, "Photon Flow For Pulse Oximetry," Sep. 15, 1995, Web Article: http://www.llnl.gov/bbrp/healthcare/projects/pfpulseoxim.html.

Heathgate Data Corp., "Pulse Oximetry," Jun. 13, 1997, Web Article: http://www.healthgate.com/healthgate/free/dph/static/dph.0200.shtml.

Jobes, et al., "Monitoring of Arterial Hemoglobin Oxygen Saturation Using a Tongue Sensor," Anesthesia & Analgesia, Feb., 1988, vol. 67, pp. 186–188.

O'Leary, et al., "Buccal Pulse Oximeter Is More Accurate Than Finger Pulse Oximeter in Measuring Oxygen Saturation," Anesthesia & Analgesia, Oct., 1992, vol. 75, pp. 495–498.

(List continued on next page.)

*Primary Examiner*—Eric F. Winakur
(74) *Attorney, Agent, or Firm*—Elizabeth Arwine; Charles H. Harris (57) ABSTRACT

A method for taking reflectance oximeter readings within the nasal cavity and oral cavity and down through the posterior pharynx. The method utilizes a reflectance pulse oximeter sensor that preferably is resistant to bodily fluids to contact one of these capillary beds for the taking of readings and then forwarding of these readings to an oximeter for display. The method includes inserting a reflectance pulse oximeter sensor into a cavity within a subject's skull and contacting a capillary bed disposed in the cavity with the reflectance pulse oximeter sensor.

12 Claims, 8 Drawing Sheets

U.S. PATENT DOCUMENTS

| | | |
|---|---|---|
| 4,112,936 | 9/1978 | Blachly . |
| 4,198,970 | 4/1980 | Luomanen . |
| 4,222,391 | 9/1980 | Rawson et al. . |
| 4,270,531 | 6/1981 | Blachly et al. . |
| 4,495,945 | 1/1985 | Liegner . |
| 4,586,513 | 5/1986 | Hamaguri . |
| 4,621,643 | 11/1986 | New, Jr. et al. . |
| 4,624,572 | 11/1986 | Van Den Bosch . |
| 4,651,746 | 3/1987 | Wall . |
| 4,676,240 | 6/1987 | Gardy . |
| 4,700,708 | 10/1987 | New, Jr. et al. . |
| 4,796,636 | 1/1989 | Branstetter et al. . |
| 4,830,014 | 5/1989 | Goodman et al. . |
| 4,854,699 | 8/1989 | Edgar, Jr. . |
| 4,859,057 | 8/1989 | Taylor et al. . |
| 4,865,038 | 9/1989 | Rich et al. . |
| 4,867,557 | 9/1989 | Takatani et al. . |
| 4,880,304 | 11/1989 | Jaeb et al. . |
| 4,890,619 * | 1/1990 | Hatschek ............................... 600/323 |
| 5,040,539 * | 8/1991 | Schmitt et al. ....................... 600/340 |
| 5,069,214 | 12/1991 | Samaras et al. . |
| 5,090,410 | 2/1992 | Saper et al. . |
| 5,193,544 * | 3/1993 | Jaffe ..................... 600/323 |
| 5,197,875 | 3/1993 | Nerli . |
| 5,203,329 | 4/1993 | Takatani et al. . |
| 5,205,281 | 4/1993 | Buchanan . |
| 5,217,012 | 6/1993 | Young et al. . |
| 5,226,417 | 7/1993 | Swedlow et al. . |
| 5,246,003 | 9/1993 | Delonzor . |
| 5,282,464 | 2/1994 | Brain . |
| 5,318,017 | 6/1994 | Ellison . |
| 5,329,922 | 7/1994 | Atlee, III . |
| 5,337,744 | 8/1994 | Branigan . |
| 5,355,874 | 10/1994 | Bertram . |
| 5,357,954 | 10/1994 | Shigezawa et al. . |
| 5,361,757 | 11/1994 | Smith et al. . |
| 5,413,101 | 5/1995 | Sugiura . |
| 5,417,207 | 5/1995 | Young et al. . |
| 5,494,032 | 2/1996 | Robinson et al. . |
| 5,595,176 | 1/1997 | Yamaura . |
| 5,596,986 | 1/1997 | Goldfarb . |
| 5,619,992 | 4/1997 | Guthrie et al. . |
| 5,638,593 | 6/1997 | Gerhardt et al. . |
| 5,655,519 | 8/1997 | Alfrey . |
| 5,673,693 | 10/1997 | Solenberger . |
| 5,678,544 | 10/1997 | Delonzor et al. . |
| 5,715,816 | 2/1998 | Mainiero et al. . |
| 5,743,261 | 4/1998 | Mainiero et al. . |
| 5,755,226 * | 5/1998 | Carim et al. ......................... 600/323 |
| 5,797,841 | 8/1998 | Delonzor et al. . |
| 5,800,349 | 9/1998 | Isaacson et al. . |
| 5,817,009 | 10/1998 | Rosenheimer et al. . |
| 5,839,439 | 11/1998 | Nierlich et al. . |
| 5,954,050 | 9/1999 | Christopher . |
| 5,983,120 * | 11/1999 | Groner et al. ....................... 600/310 |
| 5,991,648 | 11/1999 | Levin . |

OTHER PUBLICATIONS

Cote, et al., "Tongue Oximetry in Children with Extensive Thermal Injury: Comparison with Peripheral Oximetry," Can. Journal Anaesth., May, 1992, vol. 39, Issue 5, pp. 454–457.

Reynolds, et al., "Influence of Sensor Site Location on Pulse Oximetry Kinetics in Children," Anesthesia & Analgesia, 1993, vol. 76, pp. 751–754.

Faisst, et al., "Reflectance Pulse Oximetry in Neonates," European Journal of Obstetrics & Gynecology and Reproductive Biology, Aug., 1995, vol. 61, pp. 117–122.

Sheridan et al., "Intraperative Reflectance Oximetry in Burn Patients," Journal of Clinical Monitoring, Jan. 1995, vol. 11 (1): 32–34.

Faisst et al., "Intrapartum Reflectance Pulse Oximetry: Effects of Sensor Location and Fixation Duration on Oxygen Saturation Readings," Journal of Clinical Monitoring, Sep. 1997, vol. 13 (5): 299–302.

Izumi et al., "Accuracy and Utility of a New Reflectance Pulse Oximeter for Fetal Monitoring During Labor," Journal of Clinical Monitoring, Mar. 1997, vol. 13 (2): 103–108.

* cited by examiner

METHOD FOR MONITORING ARTERIAL OXYGEN SATURATION

This application claims priority from U.S. provisional Application Ser. No. 60/099,579, filed Sep. 9, 1998, U.S. provisional Application Ser. No. 60/101,079, filed Sep. 18, 1999, and U.S. provisional Application Ser. No. 60/101,143, filed Sep. 18, 1998, which are all hereby incorporated by reference.

I. FIELD OF THE INVENTION

This invention is directed to a method for measuring blood oxygenation in multiple internal areas of a subject through either the nasal cavity or the oral cavity. More particularly, the invention relates to using pulse oximeter sensors to perform reflective pulse oximetry internal to a subject.

II. BACKGROUND OF THE INVENTION

With a few exceptions, tradition and technology have favored transillumination pulse oximetry in the operating theater. The principle of operation of the pulse oximeter is fairly simple but is arguably the most important development in anesthesia monitoring in the twentieth century. Two wavelengths of light (usually 660 nm and 940 nm) are used to spectrophotometrically determine the ratio of oxidized to reduced hemoglobin noninvasively as well as to determine the pulsatility of blood plethysmographically. Presently, the most common application of this in the operating theater is via transillumination through the capillary bed of a peripheral digit. However, it is not unusual for multitrauma and thermally injured patients to either have severe peripheral vasoconstriction or to have severely damaged (or missing due to amputation) peripheral vascular beds. Reflectance oximetry rather than transillumination oximetry was the earliest investigative form of the technique. Transillumination pulse oximetry, without question, is the most effective form when oximetry is obtained through skin. However, when skin is not interposed as a barrier to capillary bed access, reflectance pulse oximetry easily can be achieved with very accurate results. The effect is achieved by the backscattering of incident bispectral light that traverses and, on reflection from nonabsorptive collagenous tissues, retraverses formed elements in the blood back to the oximetric detector. Rather than superseding transillumination pulse oximetry, this technique broadens the scope of possible monitoring sites, adding to the clinician's armamentarium.

Conventional pulse oximetry in the severely burned patient can be a significant hallenge, yet this monitoring data is vital in operating room and intensive care settings. Most current oximetric approaches depend upon available peripheral sites permitting transillumination oximetry and indeed, this method is sufficient for most surgical conditions and procedures. Unfortunately, patients with severe burns often have few sites for the effective placement of the transilluminating pulse oximeter sensor. In addition, these patients often have severe circulatory compromise rendering the peripheral pulse oximeter less efficient. A variety of studies have shown that central pulse oximeters are more reliable and rapidly responsive than peripheral pulse oximeters.

Reflectance oximetry can be a useful tool where a capillary bed is easily accessible. Indeed, it is used commonly and effectively among intrapartum and neonatal patients whose capillary beds are easily accessed through their skin. The technique has also been applied to adult and pediatric burn patients by placing the reflectance sensor in wounds or over hyperemic sites such as healed partial thickness burns.

Prior pulse oximeter sensors inserted through the mouth are usable only when the patient is under general anesthesia. These pulse oximeter sensors are inserted to reach the larynx area, for example, U.S. Pat. No. 5,282,464 to Brain et al. Another known method uses transillumination pulse oximetry of the posterior tongue, but this method may not be used with a patient, who is awake, for example, U.S. Pat. No. 5,205,281 to Buchanan. Also, the posterior tongue is not the most accessible body part to take oximetric measurements.

Recent studies indicate that oral pulse oximetry is a superior modality when compared to peripheral transillumination pulse oximetry. A variety of studies have shown that oral pulse oximeters are more reliably and rapidly responsive than peripheral pulse oximeters. However, these studies use oral transillumination pulse oximetry, held in place via complex devices or pieces of improvised malleable metal. Oral secretions, equipment failure, and placement difficulty often render these techniques ineffective.

There are other often overlooked capillary beds readily accessible in most adult burn patients that are as amenable to reflectance oximetry as the forehead of the premature infant. The buccal surface, posterior soft palate, hard palate and proximal posterior pharynx of a burned patient are seldom compromised no matter how severe the burn, and the capillary beds are very close to the surface in those areas. Transillumination pulse oximetry of the tongue and cheek has been documented as a viable method of monitoring, but not everyone has the equipment available to place a transilluminating pulse oximeter on the tongue or cheek. A reflectance pulse oximeter sensor has the bispectral emitter and the detector in a side-by-side configuration rather than in opposition. The device may be placed flat upon a suitable capillary bed and it thus becomes a reflectance pulse oximeter sensor.

The nasal mucosa and the posterior pharynx contain rich capillary beds ideal for reflectance pulse oximetry. Known pulse oximeters are not suitable for use in the nares as they tend to block the nasal passage thus constricting the patient's breathing. In addition, they are prone to difficulties when their electrical components are exposed to liquid, moisture, bodily fluids, and/or surgical fluids. Since they rely on transillumination they also tend to be difficult to hold in place.

Notwithstanding the usefulness of the above-described devices, and the above-identified recognized viability of transilluminating buccal pulse oximetry, a need exists for a more convenient method for obtaining oximeter readings from a subject.

III. SUMMARY OF THE INVENTION

The invention while addressing the problems of the prior art obtains advantages that were not achievable with the prior art methods.

An object of this invention is to provide an effective method for taking pulse oximetry measurements from nasal, oral, and posterior pharyngeal capillary beds.

Another object of the invention is the use of reflectance pulse oximetry via the nasal and/or oral cavities for a variety of surgical, anesthetic, or critical care procedures or situations to include patients that are awake, sedated or undergoing general anesthesia.

Another object of the invention is to allow for lingual placement of a pulse oximeter sensor for reflectance readings to provide efficient and clinically accurate pulse oximetry measurements.

Another object of the invention is to allow for buccal placement of a pulse oximeter sensor for reflectance readings to provide efficient and clinically accurate pulse oximetry measurements.

Still another object of the invention is to monitor oxygen levels in severely burned ICU patients who are difficult to monitor.

An advantage of the invention is an improvement in the quality of care resulting from using a straightforward method with easily used devices to take internal oximetry measurements and readings.

Another advantage of the invention is that EMS crews and personnel will be able to use this invention easily in the field during, for example, emergency situations.

Another advantage of the invention is improved pulse oximetry readings.

Another advantage of the invention is reflectance pulse oximetry requires less power to function and thus less heat is produced than transilluminance pulse oximetry. The decrease in produced heat lowers the risk the subject will be burned.

The method accomplishes the above objectives and achieves the advantages. The method is easily adapted to a wide variety of situations.

Furthermore, intraoral buccal or proximal posterior pharyngeal/palatal placement of a pulse oximeter probe in a configuration relying upon reflectance will provide pulse oximetry measurements comparable to those obtained by peripheral pulse oximetry. Test protocols suggest that buccal and proximal posterior pharyngeal/palatal reflectance pulse oximetry provides a simple, accurate means of monitoring arterial oxygen saturation in the severely burned patient where oximetric monitoring presents a challenge.

Furthermore, the method is extremely useful in cases where it is difficult at best or not even possible to attach prior art pulse oximeter sensors with clips or straps to the patient. The types of patients that this method would be useful with are critically ill or injured patients including burn or trauma patients without alternative sites and maxillofacial injuries.

Given the following enabling description of the drawings, the method should become evident to a person of ordinary skill in the art.

DETAILED DESCRIPTION OF THE INVENTION

Like reference numerals in the figures represent and refer to the same element or function.

a. Overview

In accordance with the present invention, there is a method to take oximeter readings from different sites within a subject, which may be either human or animal, for the purposes of determining the amount of oxygen within the blood of the subject. The oximeter readings are accomplished using reflectance oximetry from capillary beds that are readily accessible within the subject. The capillary beds include, for example, the nasal mucosa, the nasal passageway, the posterior pharynx, the hard palate, the soft palate, the superior lingual surface, the inferior lingual surface, the gingivae, the mouth floor, and the buccal surface. Each of these capillary beds is accessible through at least one opening in the subject's head leading to an intrahead cavity, which includes an oral cavity and a nasal cavity. The oral cavity extends from the lips to the oral portion of the pharynx, i.e., pars oralis. The nasal cavity extends from the nostrils to the nasal portion of the pharynx, i.e., pars nasalis. The nasal cavity and the oral cavity together form what is known as the nasal oral pharynx region of an individual.

Figure 1:
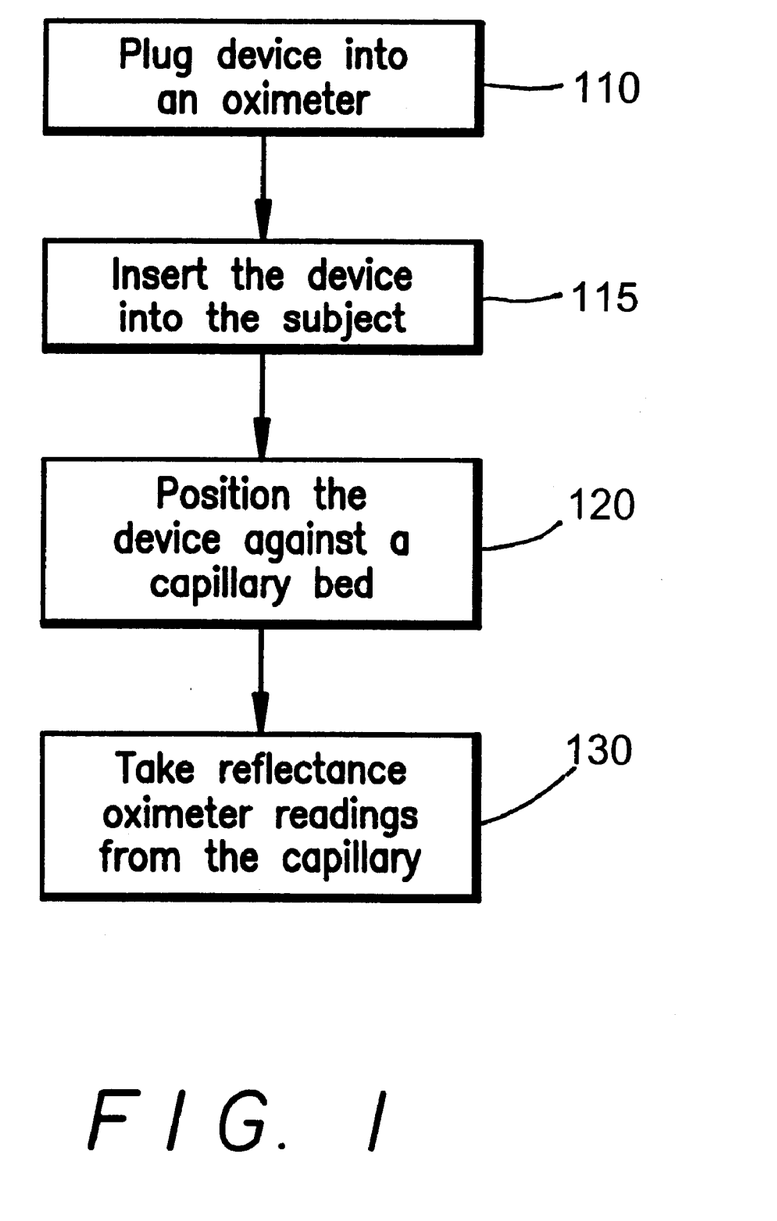
FIG. 1 illustrates a flowchart illustrating the steps for performing the preferred embodiment.

FIG. 1 illustrates a flowchart showing the common steps for taking oximeter readings from the previously mentioned capillary beds. In the first step 110, which may actually occur at a later point but no latter then the initiation of taking pulse oximeter readings, the pulse oximeter sensor elements are connected to an oximeter device such as a spectrophotometer. In step 115, the oximeter sensor device is inserted into the subject through an available opening such as the mouth or the nose. In step 120, the pulse oximeter sensor is positioned adjacent the relevant capillary bed such that the pulse oximeter sensor elements are facing and preferably in contact with the capillary bed to allow for reflectance pulse oximetry. The placement of a device with a pulse oximeter sensor is illustrated, for example, in FIGS. 2–5. In step 130, reflectance pulse oximeter readings are taken from the relevant capillary bed. While taking the pulse oximeter readings, the pulse oximeter sensor elements preferably remain in contact with the relevant capillary bed to continue the flow of accurate oximeter readings.

Figure 2:
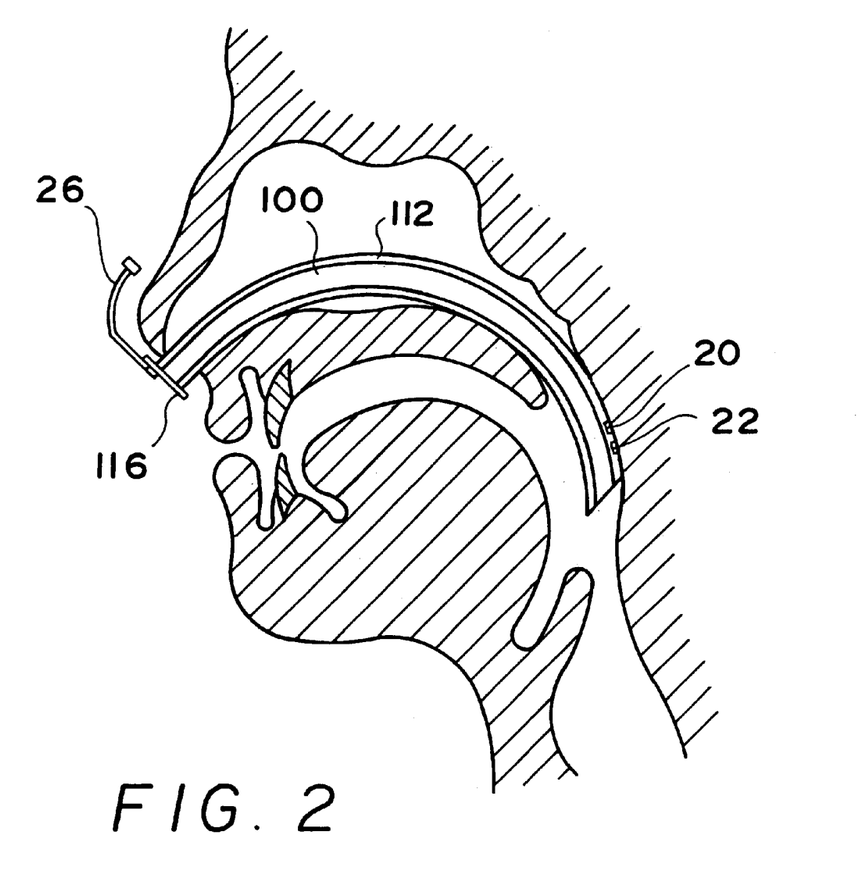
FIG. 2 depicts the nasopharyngeal airway oximeter sensor being used in the method against the posterior pharynx.
Figure 3:
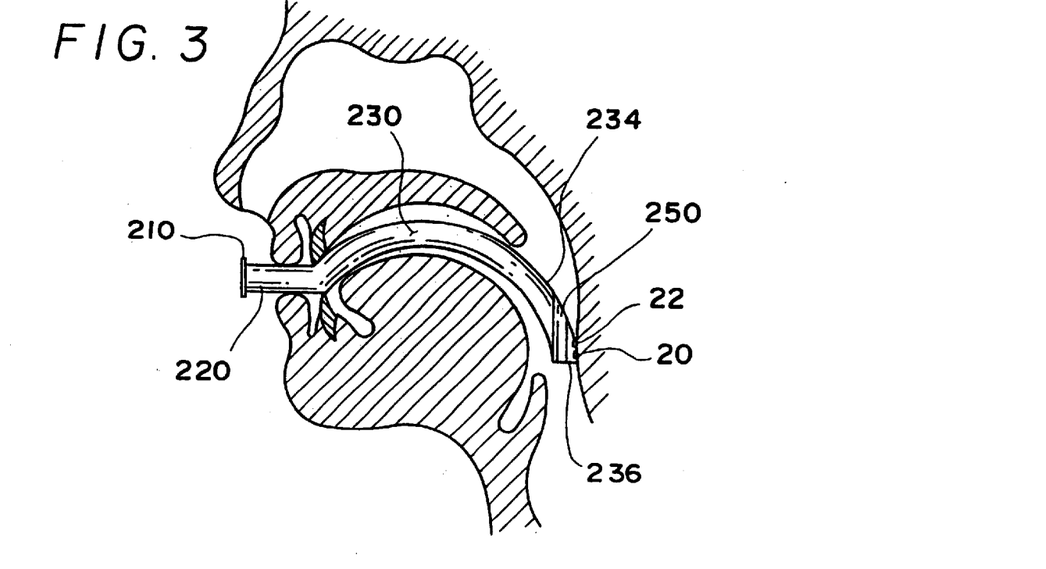
FIG. 3 illustrates the oral airway oximeter sensor being used in the method against the posterior pharynx.

In the case where the capillary bed is the nasal mucosa, the opening through which the pulse oximeter sensor is inserted is one of the nostrils as shown in FIG. 2. In the case where the capillary bed is the posterior pharynx, the pulse oximeter sensor may be inserted through either the nasal cavity or orally depending of the type of device used as exemplified by the devices shown in FIGS. 2 and 3. If the capillary bed is the soft or hard palate, the superior lingual, or the buccal surface, then the pulse oximeter sensor preferably is inserted into the mouth as shown, for example, in FIGS. 3–5.

The readings may be taken with a variety of devices, some of which are discussed below and shown in FIGS. 2–21. Suitable devices for performing the method preferably include at a minimum, the following: pulse oximeter sensor elements, including a light source and a light detector, and a support surface or structure. In addition, the devices may include wiring and an external cord, both of which may be connected to the pulse oximeter sensor elements.

More particularly, in an exemplary device, the pulse oximeter sensor elements include a light source 20, which preferably emits light with wavelengths of 660 nm (red) and 940 nm (near infrared), and a light detector 22. The placement and location of the light source 20 and the light detector 22 depicted in the Figures may be switched with respect to each other.

The light source 20 emits at least two frequencies of light at, for example, about 660 nm and about 940 nm. The light source 20 preferably is one or more of the following: two light emitters such as light emitting diodes (LED), a bispectral emitter, a dual spectral emitter, a photoemitter, or a semiconductor die. However, any light source that facilitates reflectance pulse oximetry may be employed. Typically, the two emitter arrangement will include a red LED around or at 660 nm and a near-infrared LED emitting in the range of 890 to 950 nm and more particularly at about 940 nm. The light source 20 may emit light having a bandwidth, for example, in the range of 20 to 50 nm.

The light detector 22 detects light emitted by the light source 20. Electrical signals representing the detected light are transmitted by the light detector 22 to a spectrophotometer, or other similar oximeter device, that discriminates between the relative intensity of these emissions and provides an index as to the degree of oxygen saturation of hemoglobin in blood. Preferably, the light detector 22 may be one of the following: a photoelectric receiver, a photodetector, or a semiconductor die.

Wiring 24 includes conductive lines and contact electrodes. An external cord 26 preferably is insulated and connects to the wiring 24 at the proximal end of the support structure so that the external cord 26 preferably is either outside the subject or near the opening in which the device was inserted. The external cord 26 has a standard plug design to interface with a pulse oximetry spectrophotometer, a pulse monitor such as a plethysmograph, or other external device. The spectrophotometer provides the electrical signals for controlling the pulse oximeter elements 20 and 22. The light source 20 and the light detector 22 may be in wireless communication with the external device instead of connected with the external cord 26 shown, for example, in FIGS. 3, 14, and 15.

The method according to the invention may be used in a variety of surgical, anesthetic, combat or critical care procedures or situations that include patients that are awake, sedated or undergoing general anesthesia. In particular, the method may be used throughout the pre-induction, throughout induction, during, upon emergence from, and after anesthesia without switching devices. This advantage is accomplished while avoiding uncomfortable stimulation deep in the throat, thus minimizing the possibility of gagging, vomiting, aspiration, and impingement of the teeth upon the endotracheal tube prior to extubation.

The following devices are capable of being used in conjunction with the method for at least one of the previously discussed capillary beds. Each of the discussed devices are more fully described in co-pending patent applications filed by the inventors as well be referenced below. With each device there is an explanation as to how the device is utilized in conjunction with the method.

b. Nasopharyngeal Airway Oximeter Sensor

The first device is a nasopharyngeal airway with a reflectance pulse oximeter sensor described in a co-pending patent application claiming priority from U.S. provisional Application Ser. Nos. 60/099,579 and 60/101,143. FIGS. 2 and 6–9 illustrate this device. This device includes a nasopharyngeal airway 100 in combination with pulse oximeter elements 20 and 22, wiring 24, and external cord 26. The pulse oximeter sensor elements 20 and 22 and wiring 24 are preferably disposed within the wall of the nasopharyngeal airway 100.

Figure 6:
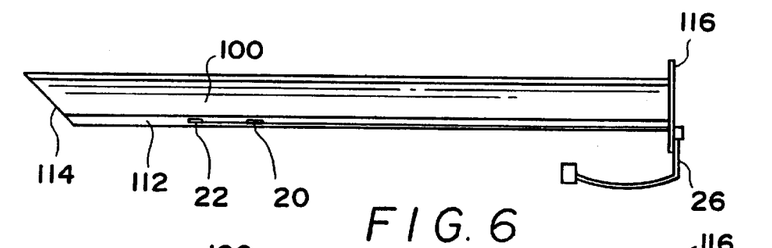
FIG. 6 depicts the nasopharyngeal airway oximeter sensor.
Figure 7:
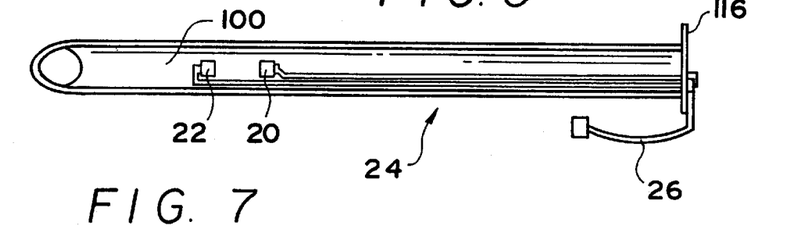
FIG. 7 illustrates a bottom view of the nasopharyngeal airway oximeter sensor.
Figure 8:
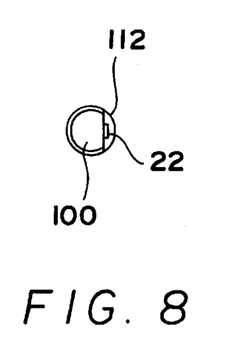
FIG. 8 depicts a radial cross-section view of the nasopharyngeal airway oximeter sensor.
Figure 9:
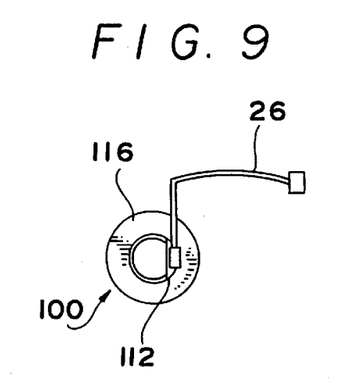
FIG. 9 illustrates a rear view of the nasopharyngeal airway oximeter sensor.
Figure 10:
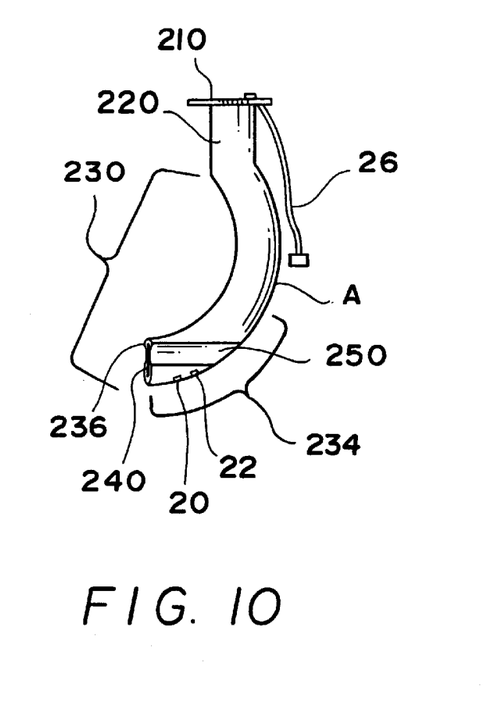
FIG. 10 depicts a side view of the oral airway oximeter sensor.
Figure 11:
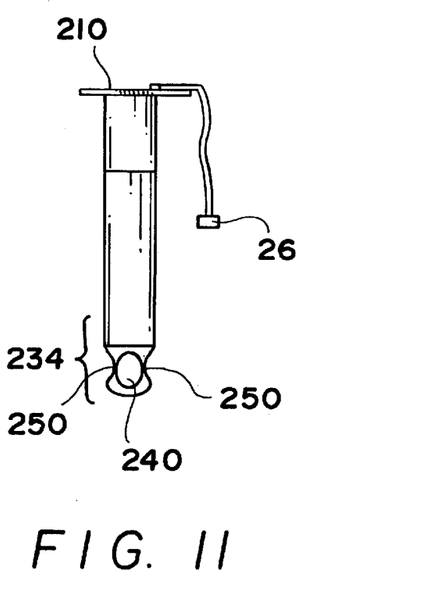
FIG. 11 illustrates a front view of the oral airway oximeter sensor.
Figure 12:
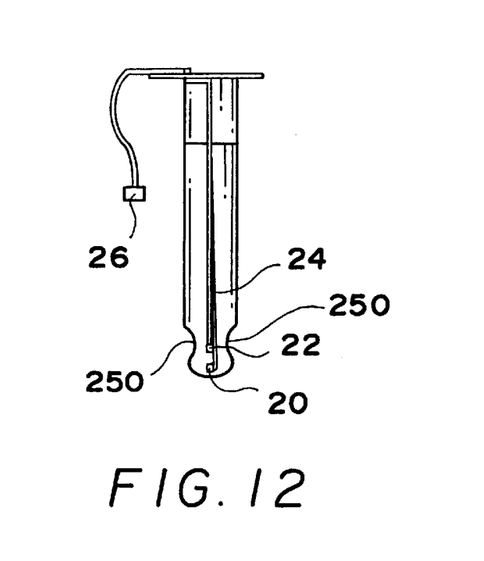
FIG. 12 depicts a rear view of the oral airway oximeter sensor.
Figure 13:
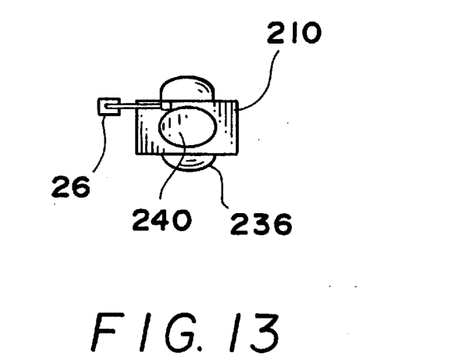
FIG. 13 illustrates a top view of the oral airway oximeter sensor.

As depicted in FIG. 6, the nasopharyngeal airway 100 is preferably a hollow, elongated member defining a passageway, e.g., a cylindrical tubular member, having an insertion end 114 and a base end (or proximal end) 116. The insertion end 114 preferably is angled. The base end 116 may be flat and disposed substantially perpendicular to the rest of the nasopharyngeal airway or angled. The base end 116 may include a notch or other marking corresponding to the tip of the nasopharyngeal airway 100 to assist the user in further positioning the device in the patient after insertion of the device.

Preferably, the wall of the nasopharyngeal airway 100 is made of a clear polymer. Furthermore, it is preferable that the wall may include a thickened section 112 around approximately one-third of the cross-sectional circumference to house the pulse oximeter sensor elements 20 and 22 and wiring 24. Alternatively, the thickened section 112 may be around just the elements and not run the length of the nasopharyngeal airway 100. The pulse oximeter sensor elements 20 and 22 and wiring 24 are preferably embedded and sealed in the wall of the nasopharyngeal airway with a cover, which may be integrally formed with the nasopharyngeal airway 100, protecting them. Preferably, the cover is a clear, fluid impermeable plastic.

Alternatively, the pulse oximeter sensor elements 20, 22, and 24 may be disposed within the passageway of the nasopharyngeal airway 100. A disposable pulse oximeter like the Nellcor® Oxisensor® II N-25 or D-25 (Nelicor Puritan Bennett®, Inc., Pleasanton, Calif.) may be stripped of its surroundings to leave only the pulse oximeter sensor elements. The pulse oximeter elements may then be fed into the nasopharyngeal airway 100 along one side of the passageway. Even though the pulse oximeter sensor elements and wiring may be present in the passageway, there is sufficient airflow capacity to supply adequate oxygen to the patient.

Preferably, the pulse oximeter sensor elements 20 and 22 are located near the angled end 114 to facilitate readings being taken from the proximal posterior pharynx as shown in FIG. 2. This arrangement provides for easy access and a reliable contact point. However, if the pulse oximeter sensor elements 20 and 22 are located near the base end 116, then the readings will be taken from within the nasal cavity. The nasal cavity, while adequate, provides less reliable and accurate pulse oximetry readings than the posterior pharynx.

The nasopharyngeal airway preferably is manufactured using polypropylene, polyvinyl chloride, silicones, epoxies, polyester, thermoplastics, rubber, similar flexible material, etc. The material should be sufficiently flexible that it freely bends in accordance with the contour of the nasal passageway. The thickened area is preferably formed from a clear or semi-translucent material to allow for the passage of light from the light source 20 and to the light detector 22.

In use, the nasopharyngeal airway 100 preferably takes measurements from a central measurement site, namely the proximal posterior pharynx, posterior soft palate or nasal mucosa. The data collected from these locations has proven more reliable then data attainable from periphery locations. The increased reliability is believed to be due to the centrality of the measurement location and the stability of the measurement surfaces.

This device is particularly useful when the patient is awake but sedated. However, the device may be used while the patient is fully awake, during induction of anesthesia, during general anesthesia, on emergence from anesthesia and during recovery. This device will allow pulse oximeter measurements to be taken in very wet environments as the oximetric components and wiring are sealed within the polymeric envelope of the nasopharyngeal airway. This device is useful for taking pulse oximeter measurements in the field and in emergency medical areas, because the device is capable of both establishing an airway and providing pulse oximetry monitoring in a single device.

C. Oral Airway/Bite Block Pulse Oximeter Sensor

Another device suitable for performing the method according to this invention is a pulse oximeter sensor combined with a combination oral airway and bite block as illustrated in FIGS. 3–5 and 12–15 and described in a co-pending patent application entitled Pulse Oximeter Sensor Combined with a Combination Oropharyngeal Airway and Bite Block claiming priority from U.S. provisional Application Ser. Nos. 60/099,579 and 60/101,079 filed concurrently herewith.

As depicted, the device includes a base 210, a straight portion 220, and a palatal and proximal pharyngeal contour portion 230 preferably arched to be physiologically compatible with the palate and pharynx. The airway also includes oximeter elements 20 and 22, which reside in the posterior distal curvature of the device. As represented in the figures, the optional wiring 24 and external cord 26 are represented, but as discussed above may be removed in a wireless configuration. The contour portion 230 includes arched section A having an outer distal curve 234 and a distal end 236. The contour portion 230 is preferably integrally formed with straight portion 220, which includes a proximal end abutting the base 210. The base 210 preferably is large enough to allow the device to be manipulated by the user.

A central passageway or channel 240 may be formed within the device to extend from the distal end 236 to the base 210. As is apparent to one of ordinary skill in the art in view of the present disclosure, the cross-section and dimensions of the passageway 240 may be selected to maximize the airflow through the passageway without reducing the integrity of the device.

Preferably, the light source 20 and the light detector 22 are embedded in the body of the device along the outer distal curve 234 facing radially outward with a cover, which may be integrally formed with the airway, protecting them. Preferably the cover is a clear, fluid impermeable plastic. Alternatively, the pulse oximeter elements 20 and 22 may be disposed within passageway 240 adjacent the outer distal curve 234. FIGS. 3 and 10–13 depict wiring 24 connecting the pulse oximeter elements 20 and 22 to the external cord 22. The wiring 24 is preferably also embedded in the body of the contour portion 230.

The pulse oximeter elements 20 and 22 may be disposed in a variety of locations along the passageway in accordance with the desired application. Preferably, the pulse oximeter elements 20 and 22 are placed closer to the distal end 236 of the device so that the readings may be taken from the posterior pharynx area, the buccal surface, the lingual surface, the gingiva surfaces, or the mouth floor of the patient. As the pulse oximeter elements 20 and 22 are moved towards the apex of the arched section A, the readings more likely will be taken from the soft palate of the patient. The dividing line between these regions is highly dependent on the internal dimensions of the patient. However, the readings obtained from each area work equally well in terms of accuracy. Also, the closer to the apex of the arched section A the pulse oximeter elements 20 and 22 are, the more difficult it is for the device to contact the buccal surface or the lingual surface when the device is used as a bite block. When the pulse oximeter elements 20 and 22 are positioned away from the apex of the arched section A towards the proximal end abutting the base 210, the readings will be taken from the hard palate, which also will provide accurate pulse oximetry readings.

To facilitate operation of the device as a bite block, bilateral grooves (or recesses) 250 into which the teeth may fit are preferably disposed in opposing relationship to each other and formed in the contour portion 230. More preferably, the bilateral grooves extend from the distal end 236 to a point along the outer distal curve 234. The bilateral grooves 250 may be filled with a sponge-like or soft material, e.g., foam or rubber to protect the teeth. The bite block groove/recess feature is not necessary for this device to be used for monitoring arterial oxygen saturation pursuant to the preferred method.

Alternatively, the pulse oximeter elements may be disposed in the passageway. A disposable pulse oximeter sensor like the Nellicor® Oxisensor® II N-25 may be stripped of its surroundings to leave only the pulse oximeter elements. The pulse oximeter elements are then fed along the topside of the passageway 240. Although the pulse oximeter elements and wiring may be present in the passageway 240, there will be sufficient airflow capacity in the passageway to supply oxygen to the patient. The N-25 pulse oximeter sensor when installed in this manner does not overdrive as a result of the emitted brightness from the light source, because of the optical effects provided by the oropharyngeal airway.

To facilitate operation of the device as a pulse oximeter sensor, a plastic bag, protective cover or similar item may be placed around the distal end 236. This addition is particularly useful when there is excess moisture that might interfere with the operation of the pulse oximeter sensor elements.

Figure 14:
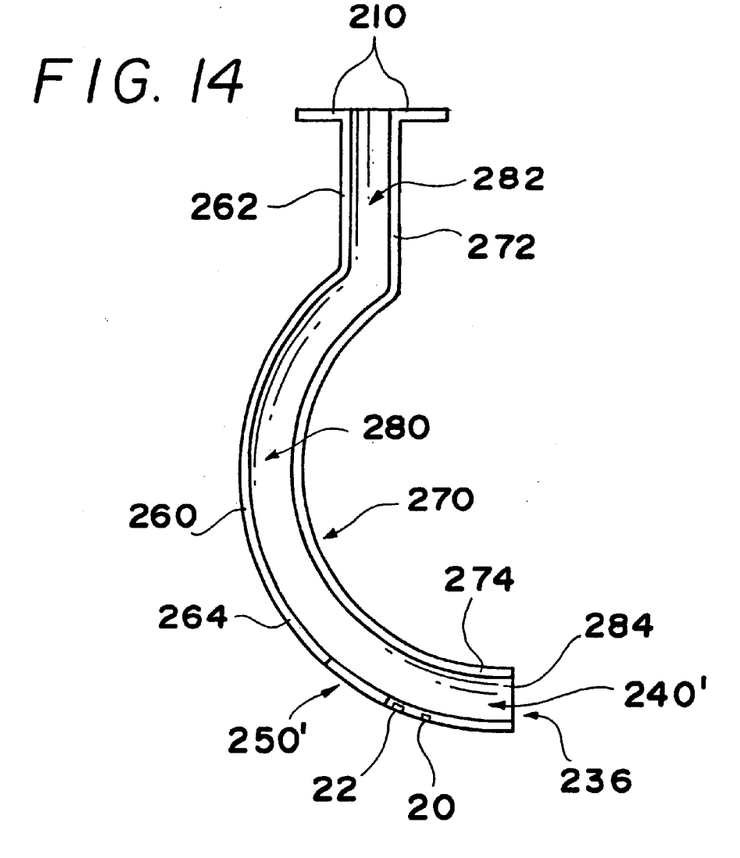
FIG. 14 depicts a side view of another oral airway oximeter sensor.
Figure 15:
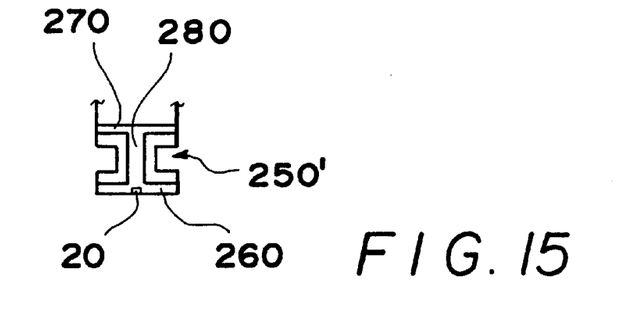
FIG. 15 depicts a partial front view of the distal end of the oral airway oximeter sensor illustrated in FIG. 14.

Alternatively the oral airway/bite block oximeter sensor may have an I-beam construction as shown in FIGS. 14 and 15. The I-beam structure includes a first wall 260, a second wall 270, and a third wall 280. The first wall 260 runs parallel to the second wall 270 and the third wall 280 runs perpendicular to and between the first and second walls 260 and 270. Each wall preferably includes a straight portion 262, 272, and 282 and a distal curve portion 264, 274, and 284 configured to fit the contour of the palatal and proximal pharyngeal. At the end opposite the distal end 236 is a base 210. A passageway 240', as shown in FIG. 14, is formed on either side of the third wall 280 and is framed by the first and second walls 30 and 40. A groove 25' may be provided in the first wall 260 to provide a recess for the teeth to pass through to facilitate operation as a bite block.

Preferably, the pulse oximeter elements 20 and 22 are located within the first wall 260 in the distal curve portion 264. Preferably, the first wall 260 is thickened in the area around the pulse oximeter elements 20 and 22 slightly relative to the second wall 270 to better house the pulse oximeter elements 20 and 22. This area may include translucent material to allow for light to travel through the first wall 260. As one of ordinary skill in the art will appreciate, the pulse oximeter elements 20 and 22 may be placed within the third wall 280 in the distal curve portion 284 (not shown). The pulse oximeter elements 20 and 22 are positioned to perform reflectance pulse oximetry. The pulse oximeter elements 20 and 22 may be placed anywhere along the length of the first and third walls 260 and 280 in a manner similar to the first oral airway/bite block oximeter sensor discussed above. The wiring 24 connected to the pulse oximeter elements 20 and 22 preferably are within the same wall as the pulse oximeter elements 20 and 22.

The base oral airway/bite block structure is preferably manufactured using polypropylene material that is either molded or extruded. Molding will produce a more rigid structure than extrusion. The sponge-like material, e.g., foam or rubber in the recesses may be added after forming the base oral airway/bite block. Both molding and extrusion will allow the pulse oximeter sensor elements to be embedded in the oral airway/bite block structure.

To accomplish a change between the two modes, this device only needs to be repositioned within the patient thus avoiding the need to exchange devices as required with present devices. For example, during anesthesia, it may be desirable to use the device as an oral airway to establish a ventilatible airway for the patient. When used as such, the device is preferably inserted into the patient's mouth such that it impinges upon the posterior soft palate and/or the posterior pharynx along the outer distal curve 234.

Figure 4:
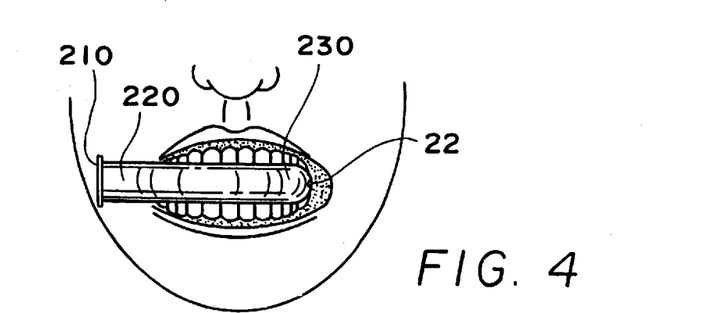
FIG. 4 depicts the oral airway oximeter sensor being used in the method against a buccal surface.
Figure 5:
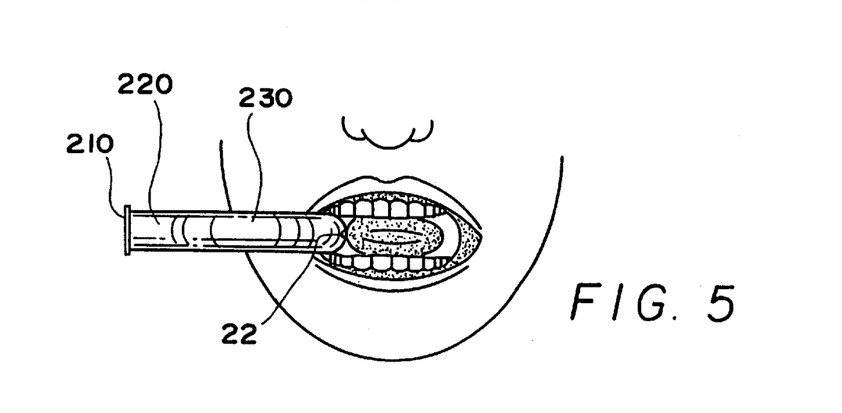
FIG. 5 illustrates the oral airway oximeter sensor being used in the method against the lingual surface.

In addition, before, on induction of, during, on emergence from and after anesthesia, it may be desirable to employ the device as a bite block. When used as such, the device is preferably inserted into the patient's mouth such that the bilateral grooves 250 on the sides of the contour portion 230 may be inserted between the molars and/or bicuspids on one side of the mouth. The outer distal curve 234 in this mode abuts the buccal mucosa, as shown in FIG. 4. The alternative preferred insertion method is to place the device such that the bilateral grooves 250 are inserted between the molars and/or bicuspids on the other side of the mouth so that the outer distal curve 234 will abut the lingual surface of the tongue, as shown in FIG. 5. Neither mode will stimulate the posterior tongue/pharynx.

d. Combination Protective Cover and Oximeter Sensor

A further device suitable for performing the method in accordance with the invention is a combination pulse oximeter sensor and protective cover as illustrated in FIGS. 16–21 and described in a co-pending patent application entitled Disposable Pulse Oximeter Assembly and Protective Cover Therefor claiming priority from U.S. provisional Application Ser. Nos. 60/099,579 and 60/101,079.

Figure 16:
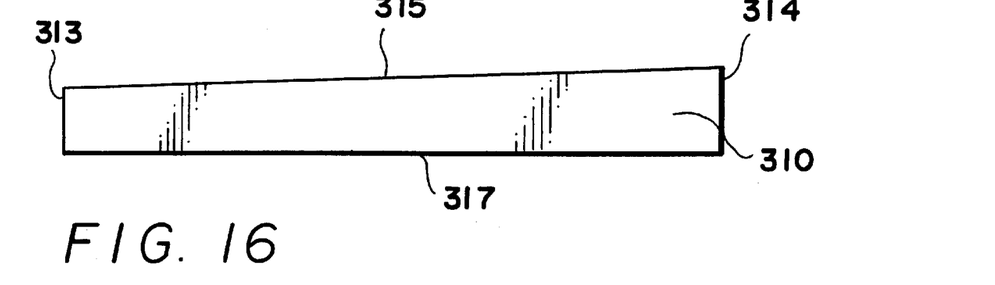
FIG. 16 illustrates a top view of a protective cover for a combined protective cover and oximeter sensor.
Figure 17:
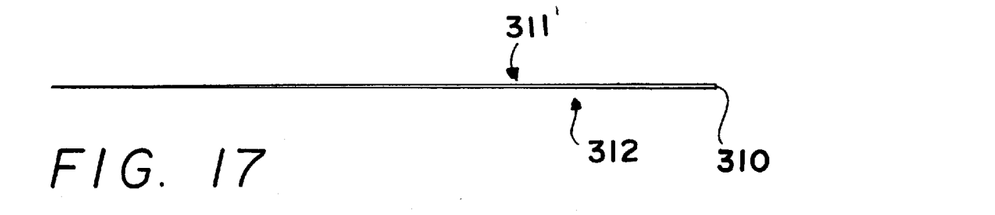
FIG. 17 illustrates a side view of the protective cover depicted in FIG. 16.
Figure 19:
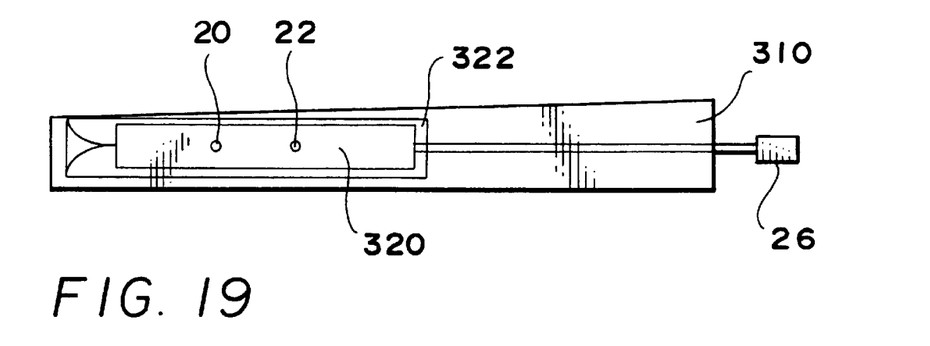
FIG. 19 illustrates a top view of the combined protective cover and oximeter sensor that may be used in the method of the preferred embodiment.
Figure 20:
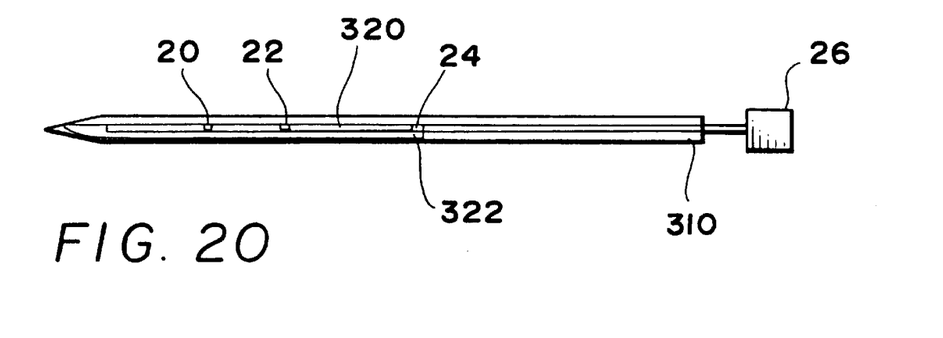
FIG. 20 depicts a side view of the combined protective cover and oximeter sensor.
Figure 21:
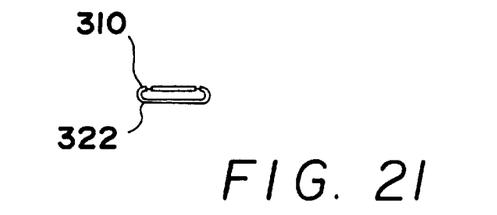
FIG. 21 illustrates an end view of the combined protective cover and oximeter sensor.

Referring to FIGS. 16 and 19, the protective covering 310 may include a condom, a shield or a protective sheath made from polypropylene, translucent rubber, or a similar material. Preferably, the protective covering 310 includes a substantially transparent section to be disposed adjacent to a light source 20 and a light detector 22 of a pulse oximeter sensor 320 that preferably includes wiring 24, an external connector 26, and plastic tape covers 322 providing the support structure. The protective covering 310 preferably includes a top surface 311 and a bottom surface 312. The protective covering 310 further includes a proximal end 314 and a distal end 313 having a pocket formed therebetween. The distal end 313 preferably is sealed while the proximal end 314 includes an opening to allow insertion of the pulse oximeter sensor 320.

The pulse oximeter sensor 320 may be disposed within the protective covering 310. To facilitate insertion, removal and storage of the pulse oximeter sensor 320 in the protective covering 310, the proximal end 314 of the protective covering 310 preferably is wider than the distal end 313. Preferably, the width of the pocket formed between the distal and proximal ends 313 and 314 increases along the length of the protective covering 310. In accordance with a particularly preferred feature of this device, the change in width of the opening along the length of the protective covering 310 is approximately one-half centimeter.

Figure 18A:
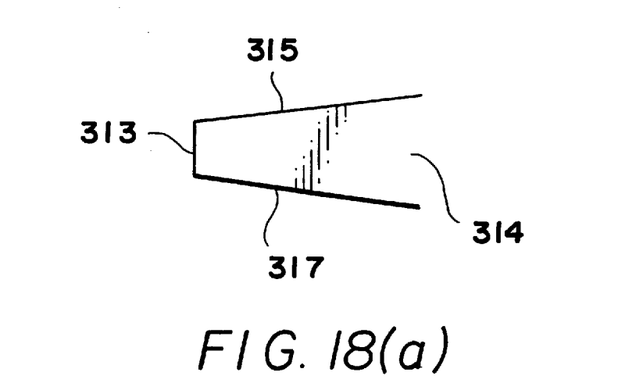
FIGS. 18(a) and 18(b) depict alternate geometries of the protective cover depicted in FIG. 16.
Figure 18B:
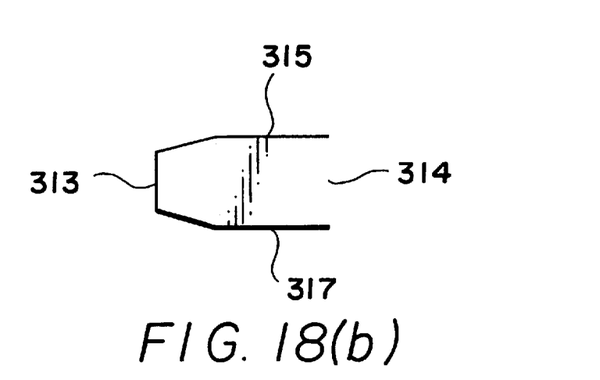

As one of ordinary skill in the art will realize from this description, the protective covering 310 may be implemented in a variety of geometries. For example, in accordance with an aspect of this device, the protective cover 10 may include first and second edges 315 and 317. As shown in FIG. 16, the first edge 315 may be angularly displaced relative to the axis of the protective covering 310. In another geometry, each of the first and second edges 315 and 317 may be angularly displaced from the axis of the protective covering as depicted in FIG. 18(a). In still another geometry, as illustrated in FIG. 18(b), the first edge 315 may include a first section that is angularly displaced from the axis of the protective covering 310 near the distal end 313 and a second section that is substantially parallel to the axis of the protective covering 310 near the proximal end 314. The second edge 317 may be a mirror image of the first edge 315 or the second edge may be parallel to the axis of the protective covering 310 along the entire length of protective covering 310 (not shown). One of ordinary skill in the art will appreciate that the forgoing constitutes only a representative sample of suitable geometries for the protective covering. Angularly displaced edges increase the convenience of using off-the-shelf pulse oximeter sensors, because the adhesive portions 322 can be folded inward without mutilating the pulse oximeter sensor by removing or excising the adhesive portions.

Furthermore, the protective covering 310 preferably is bilaminar in nature providing increased strength to contain a substantially rectangular pulse oximeter sensor 320 with probe fixing tape and/or plastic tape covers 322 folded back. The proximal end 314 may include a flap extending from either the top surface 311 or the bottom surface 312 to fold back and seal the protective covering 310 or some type of adhesive inside the pocket near the proximal end 314 to seal the protective covering 310. The protective covering 310 preferably covers and encases the pulse oximeter sensor 320 and a portion of the connector cable 24 extending from the pulse oximeter sensor 320.

In commercial applications, it is expected that the protective covering 310 will be disposable. The protective covering 310 may serve as an envelope like structure for the pulse oximeter sensor 320 to be inserted into for use. In particular, the structure of the protective covering 310 may be a blind flat bilaminar bag. As a result, the protective covering 310 insulates the pulse oximeter sensor 320 from direct contact with bodily or surgically related fluids, consequently, protecting the electrical components of the pulse oximeter sensor 320 from fluid.

The protective covering 310 is easily manufactured. Two sheets of polypropylene or similar non-reactive material may be laid out, on a substantially flat surface such that the two sheets overlap in the area where the protective covering(s) will be formed. Then, using a heat sealer or gun, the sheets may be subdivided into individual protective coverings. The heat sealer or gun allows the manufacturer to subdivide the sheets' surface area into individual protective coverings that will have their sides formed by melting together the two sheets into seams. In keeping with the invention, the two sheets of polypropylene may be replaced with a large polypropylene, or similar material, bag. In further keeping with the invention, two sheets of polypropylene may be replaced with one polypropylene, or similar material, sheet folded over such that the fold line forms the side of the protective coverings formed along the fold line.

The protective covering 310 will allow off-the-shelf disposable pulse oximeter sensors 320 to be used in a greater number of locations within patients or animals. In particular, oximetry will be able to be performed according to the invention with this device in the oral cavity on the lingual or buccal mucosa, the mouth floor, the gingiva, the hard or soft palate, or the posterior pharynx. According to this invention, the device will also be able to take oximeter readings from within the nasal cavity. An example of a disposable pulse oximeter sensors that will have increased use is the Nellcor® Oxysensor® II line of pulse oximeter probes and sensors.

The insulation aspects of the protective covering 310 will allow for use of pulse oximeter sensors 320 for peribuccal, perilingual, sublingual, peripalatal, and peripharyngeal pulse oximetry. To take readings from the buccal surface, the patient's jaw should be opened to allow access to the buccal surface. The protective covering 310 with inserted pulse oximeter sensor 320 disposed therein may be placed against the buccal surface. As the jaw closes, the muscles will contract and close around the protective covering 310, thus holding the protective covering 310 and the pulse oximeter sensor 320 against the buccal surface. A much tighter fit is possible, because of the flexible nature of the combination of the protective covering 310 and the pulse oximeter sensor 320.

e. Testing

The method of taking pulse oximeter readings from different surfaces within a patient has been submitted to actual testing in the below-described population and according to the following protocols.

Reflectance Oximetry from the Buccal Surface

The first protocol involved taking readings from the buccal surface. Nine patients were monitored via buccal reflectance pulse oximetry over 20 consecutive surgical procedures, which procedures consisted of burn excision and grafting. Patients ranged in age from 23 to 56 years (Mean=264.8, Standard Deviation (SD)=11.2) and ranged from 17 to 75 percent total body surface area (%TBSA) burned (Mean=274.3%, SD=28.9). Each patient received from one to eight operations (Mean=4.01). Five of these nine patients arrived at the operating room intubated for all of the operations in this study. Four patients were induced and intubated in a standard fashion for all surgical procedures.

A Nellcor® Oxisensor® II D-25 was placed intraoraly between the lower teeth and the left or right buccal surface of the cheek and lip, with the bispectral emitter and detector facing the buccal surface. This pulse oximeter sensor orientation was used for the duration of each case. In addition, a similar disposable oximetric probe was placed on a peripheral digit in the commonly accepted transillumination configuration. At five minute intervals throughout the case, values for both oximetric probes were coded on the anesthesia record.

The differences between the peripheral and buccal $SpO_2$ (oxygen saturation of hemoglobin) values were insignificant by t-tests for correlated means. Concordance rates as percent agreements were calculated for all cases. Average percent agreement was 84% ranging from 25% to 100%. Three of the 20 samples had percent agreements less than 91%. In each of these cases, the peripheral pulse oximeter sensor appears to have failed, in two cases secondary to sepsis, and in another secondary to peripheral vasoconstriction in the face of a norepinepherine infusion. Buccal $SpO_2$ readings in all three cases continued to be 97% or greater.

This data suggests that buccal reflectance oximetry is a simple, accurate means of monitoring arterial oxygen saturation in the severely burned patient where oximetric monitoring presents a challenge. Given that central oximetry has been shown in numerous studies to be more rapidly responsive to oxygen saturation variability than peripheral oximetry, as well as more directly reflective of central oxygen saturation, there are few drawbacks and considerable benefit from this method. Indeed, in the three examples in this study where percent agreements were low, the peripheral oximetric probes were returning apparently erratic and/or generally low values while buccal oximetric readings remained at 97% or higher. All three of these patients had peripheral vascular compromise secondary to sepsis and/or a vasoconstricting agent (norepinepherine infusion).

It may appear from the study results, at first blush, that a full range of $SpO_2$ values was not tested and that the continuously high $SpO_2$ readings are spurious to the technique. On the contrary, in order to obtain a $SpO_2$ value greater or less than 85% a very specific set of relationships must be present relative to the bispectral emitter and light sensing oximetric elements. Thus, spuriously high values in particular do not consistently occur. High $SpO_2$ values require the presence of saturated hemoglobin. Unlike lingual oximetry, this technique is not necessarily limited to intubated patients as a flat disposable oximetric probe could be placed between the cheek and teeth of an awake patient. In addition to operating room considerations, ventilated patients in intensive care settings could benefit from this technique, especially given the more rapid response of a centrally placed pulse oximeter over a peripheral one.

Posterior Pharyngeal Reflectance Oximetry

The second protocol involved comparing posterior pharyngeal reflectance pulse oximetry to conventional peripheral transillumination pulse oximetry in difficult to monitor burn patients. Eight patients' records were reviewed over fourteen consecutive surgical procedures, all consisting of excision and grafting. Patients ranged in age from 9 to 43 years and ranged from 14.5% to 77.5% TBSA burned (Mean=30.4, SD=22.1). The number of operations per patient ranged from one to four.

A Nellcor® Oxisensor® II pulse oximeter probe was placed in the distal lumen of an appropriately sized oropharyngeal airway with sensor and emitter facing the posterior pharynx. A similar probe was placed on a peripheral digit as a transilluminating pulse oximeter. $SpO_2$ values were noted at five-minute intervals. Concordance statistics as well as a t-test for correlated means were calculated between the simultaneously obtained $SpO_2$ values.

The mean differences between pharyngeal reflectance and peripheral digital transillumination $SpO_2$ values were insignificant for all cases. Concordance statistics were as follows: 0.75 (n=1) and 1.0 (n=12).

Given the near perfect concordance statistics in this study, this data suggests that posterior pharyngeal reflectance oximetry is a simple, highly accurate means of monitoring arterial oxygen saturation in the severely burned patient where oximetric monitoring presents a challenge.

Lingual Surface Reflectance Oximetry

The third protocol involved taking readings from the lingual surface. Data was reviewed for eight difficult to monitor patients who were monitored via lingual reflectance pulse oximetry over twenty-five consecutive surgical procedures, all consisting of burn excision and grafting. Patients ranged in age from 26 to 57 years (Mean=36.0, SD=10.3). Patients ranged from 20% to 92% TBSA burned (Mean=66.75%, SD=26.42). Number of operations per patient ranged from one to five (Mean 3.13, SD=1.55). Six of these eight patients arrived at the operating room intubated for all of the operations in this study. Two patients were induced and intubated in a standard fashion.

In each case, a Nellcor® Oxisensor® II D-25 was centered flat on the superior lingual surface with the detector and the bispectral emitter facing the lingual surface. This pulse oximeter configuration was used for the duration of each case. When clinically indicated, an arterial blood gas (ABG) sample was drawn and the $SpO_2$ noted for clinical monitoring and prior to transfusion in every case. All had multiple ABG's drawn and all patients were transfused. The ABG $SaO_2$ (oxygen saturation of arterial blood) was noted in each case.

Descriptive statistics and a concordance rate as well as a t-test for correlated means were calculated between the simultaneously obtained $SpO_2$ and $SaO_2$ values. The difference between the $SpO_2$ and $SaO_2$ values was insignificant by t-test for correlated means (t=1.25, df=24, NS). Upon inspection, the means were very close and the standard deviations were very small, as were the SEM's, all suggesting very little difference or variability between these two measures of oxygen saturation. A concordance rate of 92% was calculated (+1.5%) showing a high degree of relationship between lingual and ABG $SaO_2$.

This data suggests that lingual reflectance oximetry is a simple, accurate means of monitoring arterial oxygen saturation in the severely burned patient where oximetric monitoring presents a challenge. An existing disposable pulse oximeter sensor was utilized in this study saving the cost of specially designed equipment. Given that central oximetry has been shown to be more rapidly responsive to oxygen saturation variability than peripheral oximetry, there are few drawbacks and considerable benefit from this method. As a practical matter, the foregoing technique is probably limited to intubated patients, as awake, extubated patients could find the presence of a lingual pulse oximeter sensor irritating. However, this limitation would hold with lingual transillumination pulse oximetry as well. In addition to operating room considerations, ventilated patients in intensive care settings could benefit from this technique, especially given the more rapid response of a centrally placed pulse oximeter over a peripheral one.

Those skilled in the art will appreciate that various adaptations and modifications of the above-described devices and steps can be configured without departing from the scope and spirit of the their use in the method. Therefore, it is to be understood that, within the scope of the appended claims, the method may be practiced and arranged other than as specifically described herein.

What is claimed is:

1. A method for monitoring arterial oxygen saturation from an intrahead cavity site of a subject comprising:
   inserting a reflectance oximeter sensor into the subject,
   contacting the reflectance oximeter sensor against a hard palate within the subject, and
   measuring arterial oxygen saturation from the hard palate.

2. A method for monitoring arterial oxygen saturation from an intrahead cavity site of a subject comprising:
   inserting a reflectance oximeter sensor into the subject,
   contacting the reflectance oximeter sensor against a soft palate within the subject, and
   measuring arterial oxygen saturation from the soft palate.

3. A method for monitoring arterial oxygen saturation from an intrahead cavity site of a subject comprising:
   inserting a reflectance oximeter sensor into the subject,
   contacting the reflectance oximeter sensor against a proximal posterior pharynx within the subject, and
   measuring arterial oxygen saturation from the proximal posterior pharynx.

4. A method for monitoring arterial oxygen saturation from an intrahead cavity site of a subject comprising:
   inserting a reflectance oximeter sensor into the subject,
   contacting the reflectance oximeter sensor against a proximal pharyngeal surface within the subject, and
   measuring arterial oxygen saturation from the proximal pharyngeal surface.

5. A method for monitoring arterial oxygen saturation from an intrahead cavity site of a subject comprising:
   inserting a reflectance oximeter sensor into the subject,
   contacting the reflectance oximeter sensor against a gingiva surface within the subject, and
   measuring arterial oxygen saturation from the gingival surface.

6. A method for monitoring arterial oxygen saturation from an intrahead cavity site of a subject comprising:
   inserting a reflectance oximeter sensor into the subject,
   contacting the reflectance oximeter sensor against a nasal mucosa within the subject, and
   measuring arterial oxygen saturation from the nasal mucosa.

7. A method for monitoring arterial oxygen saturation from a subject comprising:
   inserting a reflectance oximeter sensor into a nasal cavity of the subject,
   contacting the reflectance oximeter sensor against a capillary bed in the nasal cavity within the subject.

8. The method of claim 7, wherein the capillary bed is on a nasal mucosa.

9. The method of claim 7, wherein the capillary bed is on a soft palate.

10. The method of claim 7, wherein the capillary bed is on a posterior pharynx.

11. A method for monitoring arterial oxygen saturation from a subject comprising:

inserting a reflectance oximeter sensor into an oral cavity of the subject, contacting the reflectance oximeter sensor against a proximal posterior pharynx surface in the oral cavity within the subject, and measuring arterial oxygen saturation from the proximal posterior pharynx.

12. A method for monitoring arterial oxygen saturation from a subject comprising:

inserting a reflectance oximeter sensor into an oral cavity of the subject, contacting the reflectance oximeter sensor against a palate in the oral cavity within the subject, and measuring arterial oxygen saturation from the palate.

* * * * *